US012728045B2

(12) United States Patent
Kalentun

(10) Patent No.: US 12,728,045 B2
(45) **Date of Patent: *Sep. 8, 2026**

(54) ABSORBENT ARTICLE

(71) Applicant: Essity Hygiene and Health Aktiebolag, Gothenburg (SE)

(72) Inventor: Pia Kalentun, Gothenburg (SE)

(73) Assignee: ESSITY HYGIENE AND HEALTH AKTIEBOLAG, Gothenburg (SE)

( * ) Notice: Subject to any disclaimer, the term of this patent is extended or adjusted under 35 U.S.C. 154(b) by 1173 days.

This patent is subject to a terminal disclaimer.

(21) Appl. No.: 16/762,856

(22) PCT Filed: Dec. 1, 2017

(86) PCT No.: PCT/SE2017/051202
§ 371 (c)(1),
(2) Date: May 8, 2020

(87) PCT Pub. No.: WO2019/108103
PCT Pub. Date: Jun. 6, 2019

(65) Prior Publication Data

US 2020/0281779 A1 Sep. 10, 2020

(51) Int. Cl.
*A61F 13/47* (2006.01)
*A61F 13/551* (2006.01)

(52) U.S. Cl.
CPC ...... *A61F 13/4704* (2013.01); *A61F 13/5513* (2013.01)

(58) Field of Classification Search
CPC ............ A61F 13/15747; A61F 13/4704; A61F 13/472; A61F 13/475; A61F 13/53409;
(Continued)

(56) References Cited

U.S. PATENT DOCUMENTS 6,350,257 B1 2/2002 Bjoerklund et al.
11,123,234 B2 * 9/2021 Vartiainen ......... A61F 13/15747
(Continued)

FOREIGN PATENT DOCUMENTS

CL 2016001725 A1 2/2017
CL 2016003034 A1 4/2017
(Continued)

OTHER PUBLICATIONS

Office Action (Decision for Patent Grant) issued on Sep. 28, 2022, by the Korean Patent Office in corresponding Korean Patent Application No. 10-2020-7018749, and an English Translation of the Office Action. (3 pages).
(Continued)

*Primary Examiner* — Catharine L Anderson
*Assistant Examiner* — Lynne Anderson
(74) *Attorney, Agent, or Firm* — BUCHANAN INGERSOLL & ROONEY PC

(57) ABSTRACT

A folded absorbent article including a fluid permeable topsheet, a backsheet and an absorbent core including at least two core layers located between the topsheet and the backsheet, an upper core layer and one or more underlying core layer(s). The upper core layer is located between the topsheet and the one or more underlying core layer(s) and the topsheet and the backsheet extend together laterally outside the absorbent core. The absorbent core has a transversal width of a transition between a front portion and an intermediate portion of the core that is narrower than a transversal width of the rest of the core. A first end portion of the article is folded about a first transversal fold line over a central area of the article, the first fold line coinciding with or being adjacent the narrow transversal transition between the front portion and the intermediate portion of the core.

22 Claims, 4 Drawing Sheets

(58) Field of Classification Search
CPC .............. A61F 13/535; A61F 13/53708; A61F 13/5513; A61F 13/5514; A61F 2013/53445; A61F 2013/53782
See application file for complete search history.

(56) References Cited

U.S. PATENT DOCUMENTS

| | | | | |
|---|---|---|---|---|
| 2003/0130643 | A1* | 7/2003 | Drevik | A61F 13/4702 604/385.31 |
| 2004/0238393 | A1 | 12/2004 | Ohi et al. | |
| 2010/0268185 | A1 | 10/2010 | Bergstrom et al. | |
| 2013/0317470 | A1* | 11/2013 | Kato | A61F 13/15747 493/405 |
| 2014/0367290 | A1 | 12/2014 | Nomoto et al. | |
| 2015/0080837 | A1 | 3/2015 | Rosati et al. | |
| 2015/0148769 | A1* | 5/2015 | Johansson | A61F 13/4757 604/385.23 |
| 2015/0173979 | A1 | 6/2015 | Carlucci et al. | |
| 2015/0313769 | A1 | 11/2015 | Dahl et al. | |
| 2015/0342796 | A1 | 12/2015 | Bianchi et al. | |
| 2020/0060887 | A1 | 2/2020 | Vartiainen et al. | |

FOREIGN PATENT DOCUMENTS

| | | | |
|---|---|---|---|
| CN | 101868209 | A | 10/2010 |
| CN | 202682195 | U | 1/2013 |
| CN | 104379105 | A | 2/2015 |
| CN | 104394819 | A | 3/2015 |
| CN | 104869964 | A | 8/2015 |
| EP | 2130522 | A1 | 12/2009 |
| EP | 2659866 | A1 | 11/2013 |
| JP | 2006149413 | A | 6/2006 |
| JP | 2010115403 | A | 5/2010 |
| JP | 2015-519154 | A | 7/2015 |
| JP | 2017074959 | A | 4/2017 |
| JP | 2017-099458 | A | 6/2017 |
| JP | 2020-501737 | A | 1/2020 |
| KR | 20000068993 | A | 11/2000 |
| KR | 20000074435 | A | 12/2000 |
| KR | 20150020681 | A | 2/2015 |
| RU | 2391080 | C2 | 6/2010 |
| WO | 0071068 | A1 | 11/2000 |
| WO | 2005048899 | A1 | 6/2005 |
| WO | 2013185800 | A1 | 12/2013 |

OTHER PUBLICATIONS

Technical Examination Report issued on Jun. 1, 2023, by the Brazilian Patent Office in corresponding Brazilian Patent Application No. BR112020009909-0, and an English Translation of the Office Action. (6 pages).

Office Action (Notification of the Second Office Action) issued on May 31, 2021 by the National Intellectual Property Administration (CNIPA) of the People's Republic of China in corresponding Chinese Patent Application No. 201780097295.0, and an English Translation of the Office Action. (13 pages).

Extended European Search Report dated Jun. 25, 2021, issued by the European Patent Office in corresponding European Application No. 17933618.5-1102, (4 pages).

Office Action issued on Jun. 29, 2021, by the Canadian Intellectual Property Office in Canadian Patent Application No. 3,083,910 (3 pages).

Office Action (Examination Report No. 1 for standard patent application) issued on Jul. 21, 2020 by the Australian Government—IP Australia in corresponding Indian Patent Application No. 2017441091. (4 pages).

Office Action (Substantive Examination Adverse Report) issued on May 25, 2022, by the Malaysian Patent Office in corresponding Malaysian Patent Application No. PI2020002352. (3 pages).

Office Action 18251 issued on Nov. 25, 2021, by the Colombian Patent Office in Colombian Patent Application No. NC2020/0006376 and an English Translation of the Office Action. (41 pages).

Chilean Search Report dated Oct. 20, 2021, issued in corresponding Chilean Patent Application No. 202001443. (39 pages).

International Search Report (PCT/ISA/210) mailed on Jul. 13, 2018, by the Swedish Patent Office as the International Searching Authority for International Application No. PCT/SE2017/051202.

Written Opinion (PCT/ISA/237) mailed on Jul. 13, 2018, by the Swedish Patent Office as the International Searching Authority for International Application No. PCT/SE2017/051202.

Office Action (Notice of Reasons for Rejection) issued on Jul. 26, 2021, by the Japanese Patent Office in corresponding Japanese Patent Application No. 2020-529554, and an English Translation of the Office Action. (7 pages).

Office Action (Decision to Grant) issued on Nov. 23, 2020 by the Federal Service for Intellectual Property in Russian Patent Application No. 2020121590/03(037065) and an English Translation of the Office Action. (20 pages).

Office Action (Notification of the First Office Action) issued on Nov. 9, 2020 by the National Intellectual Property Administration (CNIPA) of the People's Republic of China in corresponding Chinese Patent Application No. 201780097295.0, and an English Translation of the Office Action. (32 pages).

* cited by examiner

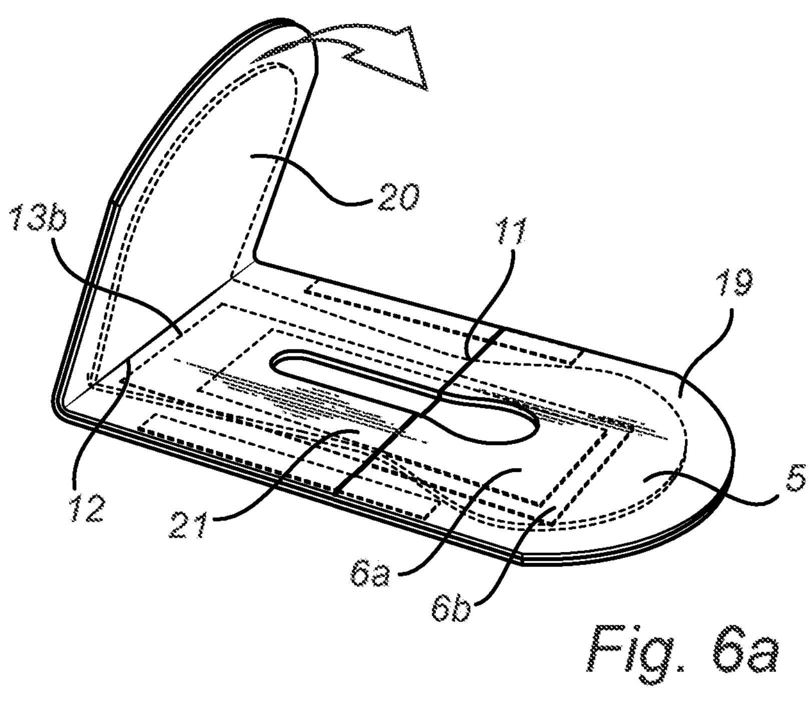
Fig. 6a
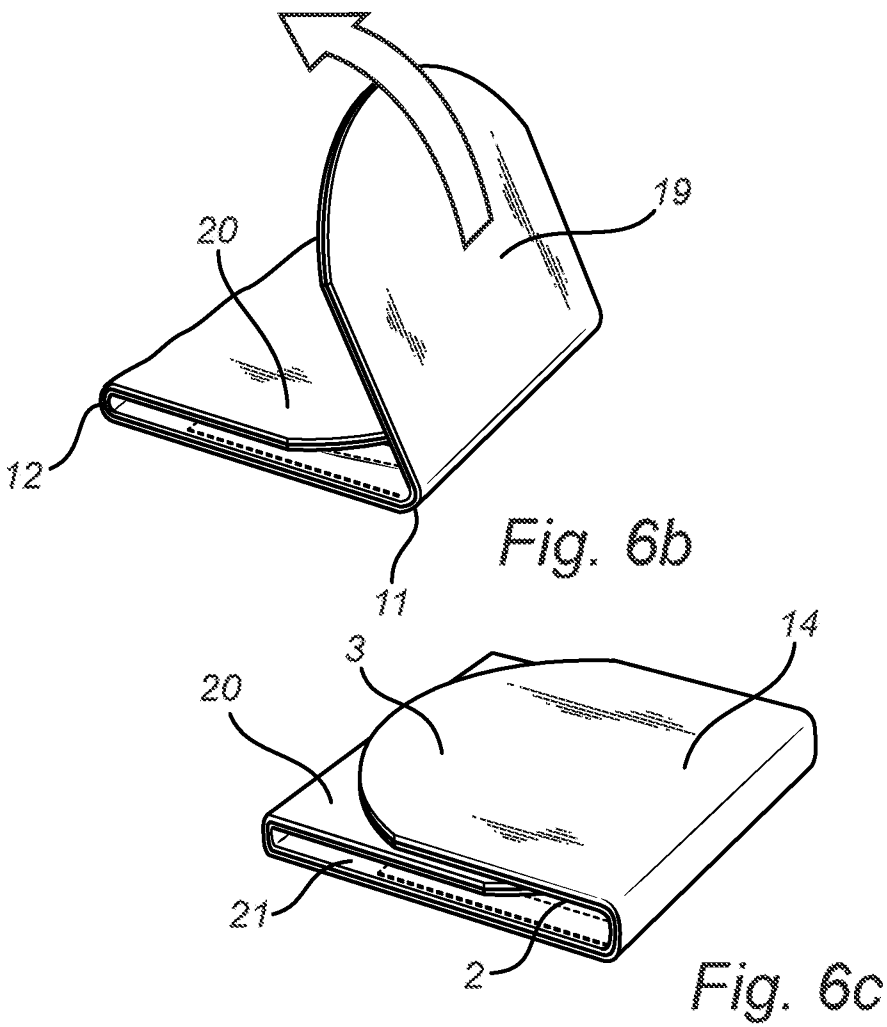
Fig. 6b
Fig. 6c

ABSORBENT ARTICLE

TECHNICAL FIELD

The present disclosure concerns a folded absorbent article such as a sanitary napkin or pad and a package comprising a plurality of folded absorbent articles. The present disclosure also concerns methods for folding an absorbent article.

BACKGROUND

Absorbent articles of the kind that is worn inside ordinary underpants include absorbent napkins or pads for adult incontinence or feminine use.

The napkins or pads are generally provided with an absorbent core to receive and retain body liquids. In order for such absorbent articles to function efficiently, the absorbent core must quickly acquire body liquids into the structure from the point of application and subsequently distribute the body liquids within and throughout the absorbent core to provide maximum leakage containment. An acquisition/distribution layer in connection to the core and an opening of the core aids when subsequent insults are directed to the same local area as previous insults, as the local area tends to be already filled with liquid from the previous insult.

As these types of articles have to be sized and configured to fit in the limited space available in the crotch portion of the underwear, a particular problem is that they may leak at the side edges, before the full absorption capacity of the article has been utilized. The fluid will instead flow on the topsheet and out over the side edges of the article where it can leak out and soil the wearer's clothing. A further drawback when fluid flows on the outside of the topsheet is that a large portion of the body-contacting topsheet will be wet. This is of course highly undesirable as it makes the article unhygienic and unpleasant to wear. It is also desirable that the article should be neat and easily foldable to obtain individual package sizes for easy bring along of the article in a bag or pocket and for easy disposal after use.

SUMMARY

It is therefore an object of an embodiment of the present disclosure to provide an improved folding and packaging solution for absorbent articles.

One or more of the above objects may be achieved with a folded absorbent article in accordance with embodiments of the present disclosure, a package comprising a plurality of folded absorbent articles in accordance with embodiments of the present disclosure or methods of folding an absorbent article in accordance with embodiments of the present disclosure. Further embodiments are set out in the following description and in the drawings.

A folded absorbent article as disclosed herein comprises a fluid permeable topsheet, a backsheet and an absorbent core comprising at least two core layers located between the topsheet and the backsheet, an upper core layer and one or more underlying core layer(s). The upper core layer is located between the topsheet and the one or more underlying core layer(s) and the topsheet and the backsheet extend together laterally outside the absorbent core. The absorbent core, in its longitudinal direction, has a front portion, a rear portion and an intermediate portion located between the front portion and the rear portion, a transversal width of a transition between the front portion and the intermediate portion of the core is narrower than the transversal width of the rest of the core. A first end portion of the article is folded about a first transversal fold line over a central area of the article, the first fold line coinciding with or being adjacent the narrow transversal transition between the front portion and the intermediate portion of the core. The upper core layer extends over the front, the intermediate and the rear portions of the absorbent core. At least one of the one or more underlying core layer(s) is shorter than the upper core layer and extends over the intermediate portion and at least a part of the front portion of the absorbent core. A second end portion of the article is folded about a second transversal fold line over the central area of the article, the second fold line being at or adjacent a rear transversal edge of the at least one shorter underlying core layer. The second fold line coincides with, or is adjacent to the transition between the intermediate portion and the rear portion of the absorbent core. The rear edge on the at least one shorter underlying core layer ends so that the shorter core layer is not part of the folding. The rear edge of the at least one shorter underlying core layer may ends within a distance of 5 mm, 3 mm, 2 mm or 1 mm before the second fold line, and thus does not form part of the fold. The first end portion is either folded onto the central area with the second end portion being folded onto the first end portion, or the second end portion is folded onto the central area and the first end portion is folded onto the second end portion.

Accordingly, the absorbent article is divided into the first end portion, the central area of the article and the rear end portion of the article by the first fold line and the second transverse fold line. In a corresponding manner, the absorbent core is divided into the front portion, the intermediate portion by the first and second transverse fold lines.

The folded absorbent article is thus a tri-folded absorbent article, with three overlapping folded portions along the length of the absorbent article.

The folding of the absorbent article about the first transverse fold line is facilitated by the fact that the first fold line coincides with the narrow transversal transition between the front and the intermediate portions having a narrower width than the rest of the core. The fact that the second fold line is at or adjacent the rear transversal edge of at least one underlying core layer(s) facilitates the folding of the second end portion. Furthermore, as at least one of the underlying core layers does not extend into the second end portion, the second end portion has a reduced thickness. Therefore, also the folded absorbent article has a reduced and homogenous thickness. The reduced and homogenous thickness of the folded absorbent articles improves the stackability of the absorbent articles in a package comprising a plurality of the folded absorbent articles. Thus a stable package with a reduced size may be achieved.

The present disclosure also relates to a package comprising a plurality of the folded absorbent articles, the absorbent articles in the package being tri-folded, as set out herein.

According to one aspect, the present disclosure relates to a method of folding an absorbent article, the article comprising a fluid permeable topsheet, a backsheet and an absorbent core comprising at least two core layers located between the topsheet and the backsheet, an upper core layer being located between the topsheet and one or more underlying core layer(s), the topsheet and the backsheet extending together laterally outside the absorbent core, the core in its longitudinal direction having a front portion, a rear portion and an intermediate portion located between the front portion and the rear portion, a transversal width of a transition between the front portion and the intermediate portion of the core being narrower than the transversal width of the rest of the core, the upper core layer extending over the front, the intermediate and the rear portion of the absorbent core, and at least one of the one or more underlying core layer(s) is shorter than the upper core layer and extends over the intermediate portion and at least a part of the front portion of the absorbent core, the method comprising:

a) folding a first end portion of the article about a first transversal fold line onto a central area of the article, the first fold line coinciding with or being adjacent the narrow transversal transition between the front portion and the intermediate portion of the core; and b) folding a second end portion of the article about a second transversal fold line onto the first folded end portion, the second fold line being at or adjacent a rear transversal edge of the at least one underlying core layer being shorter than the upper core layer.

The fact that the second end portion of the article is folded over and onto the first end portion facilitates folding of the second end part, as the transversal edge of the at least one shorter underlying core layer is located at or adjacent the second transversal fold line thus providing a natural fold line. The reduced thickness of the rear portion of the core and thus the second end portion of the absorbent article also makes the folding easier.

The fact that at least one underlying core layer is shorter and the second fold line being at or adjacent the rear end edge of the underlying core layer may cause a fold mark in the absorbent core. Such fold mark could make it more difficult to shape the absorbent core in the transition area between the rear and intermediate portion and spreading of liquid could be affected negatively in this area. The fold mark at the second fold line may become less distinct at the rear edge of the underlying shorter core layer if the first end portion is folded under the second end portion giving a u-shaped folding at the second transversal fold line.

According to a further aspect, the present disclosure relates to a method of folding an absorbent article, the article comprising a fluid permeable topsheet, a backsheet and an absorbent core comprising at least two core layers located between the topsheet and the backsheet, an upper core layer being located between the topsheet and one or more underlying core layer(s), the topsheet and the backsheet extending together laterally outside the absorbent core, the core in its longitudinal direction having a front portion, a rear portion and an intermediate portion located between the front portion and the rear portion, a transversal width of a transition between the front portion and the intermediate portion of the core being narrower than the transversal width of the rest of the core, the upper core layer extending over the front, intermediate and rear portions of the absorbent core, and at least one of the one or more underlying core layer(s) is shorter than the upper core layer and extends over the intermediate portion and at least a part of the front portion of the absorbent core, the method comprising:

a) folding a second end portion of the article about a second transversal fold line onto a central area of the article, b) folding a first end portion of the article about a first transversal fold line and onto the second folded end portion, the first fold line coinciding with or being adjacent the narrow transversal transition between the front portion and the intermediate portion of the core; and, c) the second fold line being at or adjacent a rear transversal edge of the at least one of the one of more underlying core layer(s).

The first transversal fold line thus coincides with the transition between the front and the intermediate portion of the absorbent core and the second transversal fold line coincides with the transition between the intermediate portion and the rear portion of the absorbent core.

The longitudinal extension of the rear portion and the longitudinal extension of the second end portion may be about a third of the longitudinal extension of the total longitudinal extension of the upper core layer and the total longitudinal extension of the absorbent article respectively.

The fact that the second end portion is folded at or adjacent the rear transversal edge of a shorter underlying core layer facilitates the folding, with the rear transversal edge providing support upon folding and giving the absorbent article a natural rear fold line.

It is often desired that the front and central parts of absorbent articles adopt a cup-shape to better store liquid prior to absorption of the liquid into the absorbent core. By folding the first end onto the second end portion the first transverse fold may become softer and less distinct and the front part of the absorbent article may adopt more easily a cup-shape after unfolding and during use of the absorbent article.

The absorbent article may be in the form of an incontinence pad or a sanitary napkin. The article may be for feminine or incontinence use, and may have an elongate, generally rectangular shape when fully extended in all directions. In this context, a generally rectangular shape is intended to encompass also that, for instance, the corners of the absorbent article may be rounded, or that the edges of the absorbent article may not be completely linear. The absorbent article may have two longitudinal side edges having equal length and extending generally in the same direction.

The topsheet and the backsheet of the absorbent article may extend together laterally outside the absorbent core along the whole circumference of the article and be connected to each other in an edge joint around the periphery of the absorbent core for leakage security. The topsheet may cover part of the backsheet to form an edge barrier.

The topsheet may consist of any material which is suitable for the purpose, i.e., be soft and liquid pervious. Examples of topsheet materials are nonwoven materials, perforated plastic films, plastic or textile mesh, and fluid permeable foam layers. Laminates consisting of two or more topsheet materials may also be employed, as are top sheets consisting of different materials within different parts of the fluid permeable wearer-facing surface.

The backsheet may be fluid impermeable. Backsheet materials that are only fluid repellant may be used particularly in instances where relatively small amounts of urine are expected to be taken up. The backsheet may be a thin, flexible, fluid-impermeable plastic film, such as of polyethylene or polypropylene, but fluid-impermeable nonwoven materials, fluid impermeable foams and fluid impermeable laminates are also contemplated. The backsheet may be breathable, implying that air and vapor may pass through the backsheet. Furthermore, the backsheet may have an outer, garment-facing surface of a nonwoven material.

The core in its longitudinal direction has a front portion, a rear portion and an intermediate portion located between the front portion and the rear portion, a transversal width of a transition between the front portion and the intermediate portion of the core is narrower than the transversal width of the rest of the core. A transversal width of the transition between the front portion and the intermediate portion of the core may be 50-75% of the widest width of the front portion of the absorbent core.

The absorbent core comprises at least two absorbent core layers. An upper core layer is located between the topsheet and one or more underlying core layer(s). The upper core layer extends over the front, the intermediate and the rear portions of the absorbent core, and at least one underlying core layer(s) is shorter than the upper core layer and extends over the intermediate portion and at least a part of the front portion of the absorbent core. Thus, one or more of the underlying core layer(s) may not extend into the rear portion of the absorbent core. The core layer(s) may have an extension into the front portion of the absorbent core of up to 75%, or up to 60% of the longitudinal extension of the front portion of the absorbent core.

The front portion, the rear portion and the intermediate portion of the absorbent core may be of substantially equal length. The length of each of the front portion, the rear portion and the intermediate portion of the core may each constitute 25-40% of the longitudinal extension of the absorbent core. The front portion of the at least one shorter underlying core layer(s) may constitute 20-40% of the total longitudinal extension of the shorter underlying core layer. The surface area of the at least one shorter underlying core layer may be 30-60% of the surface area of the upper core layer. The first fold line coincides with the transition between the front and the intermediate portion of the absorbent core and the second fold line coincides with the transition between the intermediate portion and the rear portion of the absorbent core.

The thickness of the rear portion of the absorbent core may be 25-70% of the thickness of the intermediate portion of the core, or may be 30-60%, or 35-50%, alleviating an easy fold. The thickness of the front portion of the absorbent core may be 25-70% of the thickness of the intermediate portion of the core, or may be 30-60%, or 35-50% alleviating an easy fold.

The absorbent core may comprise an upper core layer having an opening extending there through and an underlying core layer in the form of a fluid flow control structure located between upper core layer and said backsheet. The absorbent core may further or alternatively comprise at least one underlying core layers in the form of a fluid storage layer(s). The fluid storage layer(s) may be located between the upper core layer and the backsheet or between the fluid flow control layer and the backsheet. The absorbent core has, in its longitudinal direction, a front portion, a back portion and an intermediate portion extending between the front portion and the back portion. A narrow transversal transition is located between the front portion and the intermediate portion. The width of the narrow transversal transition may be between 50 and 75%. The opening in the upper core layer extends completely through the layer, thereby forming a cavity in the article, 80-100% or 90-100% of the longitudinal extension of the opening may be located in the front and the intermediate portion of the upper core layer in order to ensure a proper placement of the hole in relation to the wetting point of the article. About 5 to 20% of the longitudinal extension of the opening may be located in the front portion of the upper core layer. The longitudinal extension of the opening in the upper core layer may be 20-40% of the longitudinal extension of the upper core layer in order to ensure fluid flow into the opening and not on the outside of the topsheet. The transverse dimension of the opening may be larger in the front portion of the upper core layer than the transverse dimension of the opening in the intermediate portion of the upper core layer in order to improve the fluid intake rate through the hole and further into the fluid flow control structure. Thereby an absorbent article is achieved which will stay in place during use and which ensures that liquid will be directed to the opening and pass into the fluid flow control structure and the core. The upper core layer may have one opening only for both leakage security and improved feeling of safety for the user.

The width of the narrow transversal transition is preferably 50-75% of the widest transversal width of the front portion of the upper core layer in order to obtain a good hook behind the tendons of the wearer. The width of the narrow transversal transition may be 50-75%, preferably 55-70% of the widest transversal width of the back portion of the upper core layer in order to ensure an improved fit of the article. The widest transversal width of the front, intermediate and the back portion may be about 75-170 mm. The longitudinal extension of the narrow transversal transition may be 5-20% of the longitudinal extension of the upper core layer to further ensure that the article has a proper fit and stays in place during use. The width of the narrow transversal transition of the upper core layer may be less than 130 mm and larger than 30 mm, preferably less than 90 mm and larger than 50 mm for an improved fit of the article between the tendons of the wearer. The longitudinal extension of the upper core layer may be about 230-400 mm.

The absorbent core may be made up of any suitable absorbent or fluid uptake and storing materials, such as one or more fluid storage layers of for example cellulose fluff pulp. The absorbent core may contain fibers or particles of highly absorbent polymer material, commonly known as superabsorbents, which are materials having the ability to absorb and retain large quantities of fluid upon formation of a hydrogel. The superabsorbents may be mixed with cellulose fluff pulp and/or may be arranged in pockets or layers in the absorbent core. The fibres may be pulp fibres and the superabsorbent material may be polyacrylate-based particles. The absorbent structure may comprise at least 20% superabsorbents and may comprise 20-80% superabsorbents and 80-20% pulp fibres. The absorbent core may further incorporate components for improving the properties of the absorbent core. Some examples of such components are binder fibers, fluid-dispersing materials, wetness indicators, fluid acquisition materials, etc.

The absorbent core layers may be homogeneous structures or may in themselves be layered structures such as absorbent laminates of the same or different materials. The absorbent layers may have uniform thickness or may vary in thickness in different parts of the layers. Similarly, the basis weight and composition may vary within the absorbent layers. By way of example, an absorbent layer may comprise a mixture of absorbent and/or non-absorbent fibres and superabsorbent material, wherein the ratio of superabsorbent material to fibres may vary in the layer.

One of the underlying layer(s) may be a fluid flow control structure, which may be located between the upper core layer and one or more underlying core layer(s). The fluid flow control structure may be of a rectangular shape. The fluid flow control structure may have a surface extension covering the surface area of the longitudinal extension of the upper core layer. The fluid flow control structure may be surrounded in the longitudinal and lateral directions by portions of the absorbent core.

The fluid flow control structure may for example be a layered structure comprising a non-perforated fibrous polymeric layer and a first perforated polymeric layer, wherein the polymers in the first perforated polymeric layer are selected from polyolefins, polyesters, polyamides and blends and combinations thereof. The first perforated polymeric layer may have a basis weight of from 50 g/m2 to 150 g/m2, or a basis weight of from 60 g/m2 to 140 g/m2. The first perforated polymeric layer may be a nonwoven, a film or a film/nonwoven laminate. The first perforated polymeric layer may for example be a three-dimensionally formed layer having penetrating apertures. The non-perforated fibrous polymeric layer may be a high loft material of 50 g/m2 to 150 g/m2 or a basis weight of from 60 g/m2 to 140. The polymer for the non-perforated fibrous polymeric layer may be polyester. The fluid flow control structure may also be a three layer structure consisting of the non-perforated fibrous polymeric layer, the first perforated polymeric layer and a second perforated polymeric layer. The non-perforated fibrous polymeric layer may be sandwiched between the first perforated polymeric layer and the second perforated polymeric layer. The second perforated polymeric layer may also be a three-dimensionally formed layer having apertures extending from a first surface of the web towards a second surface of the web and forming protrusions on the second surface.

The fluid flow control structure may have relatively high bending stiffness. A high bending stiffness provides the absorbent article with an improved ability of resisting transverse compression between the thighs of a wearer of the article and counteracts unwanted deformation of the article during wear. The bending stiffness or flexure resistance of the laminate material in the fluid flow control structure may be 0.5-5 N, preferably 1-4 N, as measured by the modified ASTM D 4032-82 CIRCULAR BEND PROCEDURE.

The fluid flow control structure may not extend into the rear portion of the absorbent core and thereby alleviating a fold about the second fold line by providing a support and natural folding guide upon folding. Such an arrangement may be especially advantageous when the fluid flow control structure for example has a relatively high basis weight, is a laminate comprising two or more layers, and also when it has a relatively high bending stiffness.

The fluid flow control structure may have an extension in the longitudinal direction beyond the rear transversal fold line and thus beyond the extension of an underlying core layer.

The absorbent article may comprise two or more underlying core layers, one of the underlying core layers may be a fluid flow control structure, as described above and one of the underlying core layers may be a fluid storage structure, as described above. The fluid flow control structure may be located between the upper core layer and the fluid storage structure.

The fluid control structure may extend over the intermediate portion and at least a part of the front portion of the absorbent core and may be shorter than the upper core layer. The second folding line of the absorbent article may be at or adjacent the rear transversal edge of the fluid control structure, such that the rear transversal edge of the fluid control structure constitutes a support and folding guiding upon folding the absorbent article over the second folding line. Additionally, or alternatively, the fluid storage structure may be the underlying core layer being shorter than the upper core layer, such that the second folding line of the absorbent article may be at or adjacent the rear transversal edge of the fluid storage structure.

An elastic member may be arranged along each longitudinal side edge of the article, at least laterally outside of the transition between the front portion and the intermediate portion of the core. The elastic members may be located between the topsheet and the backsheet. The article may have an interspace free from absorbent material located between the elastic member and the transition between the front portion and the intermediate portion of the core, more specifically in an area between the elastics, located at the periphery of the article, and the periphery of the upper core layer. Each elastic member may have an extension at least to a lateral edge of a widest part of the front portion of the absorbent core to facilitate the fold of the first end portion of the article. The elastic member may not extend in the longitudinal direction beyond the rear transversal edge of the rear part of the shorter underlying core layer to facilitate the fold. The elastic members may not extend beyond the second fold line of the article to facilitate fold about the fold line.

The absorbent article may further include fastening means for fastening of the absorbent article inside a supporting pant garment, such as a pair of underpants. The fastening means may be covered by a releasable protective layer.

The absorbent article comprises at least two fold lines. A fold line may or may not be visible on the absorbent article. A fold line is a location of the article wherein folding is alleviated due to the construction of the article. The first transversal fold line of the article is coinciding with or adjacent the narrow transversal transition between the front portion and the intermediate portion of the core. The folding about this first fold line is facilitated by the narrow transversal transition between the front and the intermediate portions having a narrower width than the rest of the core. The second fold line is adjacent the rear transversal edge of at least one of the underlaying core layer(s), thus just beyond the longitudinal extension of at least one of the underlaying core layer(s). Adjacent as defined herein is a feature lying close or nearby another feature. The second fold line coincides with the transition between the intermediate portion and the rear portion of the absorbent core. At least one of the underlying core layer(s) has a shorter longitudinal extension than the upper core layer, which is the core layer being closest to the topsheet. The folding about the second fold line is facilitated by the relative sizes of the upper and the underlying core layer(s) and their relative positions providing less stiffness and less resistance to folding compared with other core constructions. The folding about the first and second fold lines may be further facilitated by the location of for example possible elastic members.

The first end portion of the article comprises the front portion of the core. A central area of the article comprises the intermediate portion of the core. The second end portion of the article comprises the rear portion of the core.

According to one aspect of the present invention, the first fold is accomplished by folding the first end portion of the article about a first transversal fold line onto a central area of the article, the first fold line coinciding or being adjacent the narrow transversal transition between the front portion and the intermediate portion of the core. The result of the first fold is that the topsheet of the first end portion of the article is facing the topsheet of the central area of the article. The second fold is accomplished by folding the second end portion of the article about a second transversal fold line onto the first folded end portion, the second fold line being adjacent a rear transversal edge of the first absorbent core layer. The result of the second fold is that the topsheet of the second end portion of the article is facing the backsheet of the first folded end portion of the article.

According to another aspect of the present disclosure, the first fold is accomplished by folding the second end portion of the article about the second transversal fold line onto the central area of the article, the second fold line being adjacent a rear transversal edge of the first absorbent core layer. The second fold is accomplished by folding the first end portion of the article about the first transversal fold line onto the second folded end portion, the first fold line coinciding or being adjacent the narrow transversal transition between the front portion and the intermediate portion of the core. The result of the first fold is that the topsheet of the second end portion of the article is facing the topsheet of the central area of the article. The result of the second fold is that the topsheet of the first end portion of the article is facing the backsheet of the second folded end portion of the article.

The folded absorbent article is thus a tri-folded absorbent article with three overlapping portions along the length of the absorbent article.

BRIEF DESCRIPTION OF THE DRAWINGS

The invention will be more closely described with reference to the enclosed Figures, in which:

FIGS. 6*a*-6*c* are elevation views of successive steps of an alternative folding the absorbent article of FIG. 1.

DETAILED DESCRIPTION

Figures 1, 2, 3:
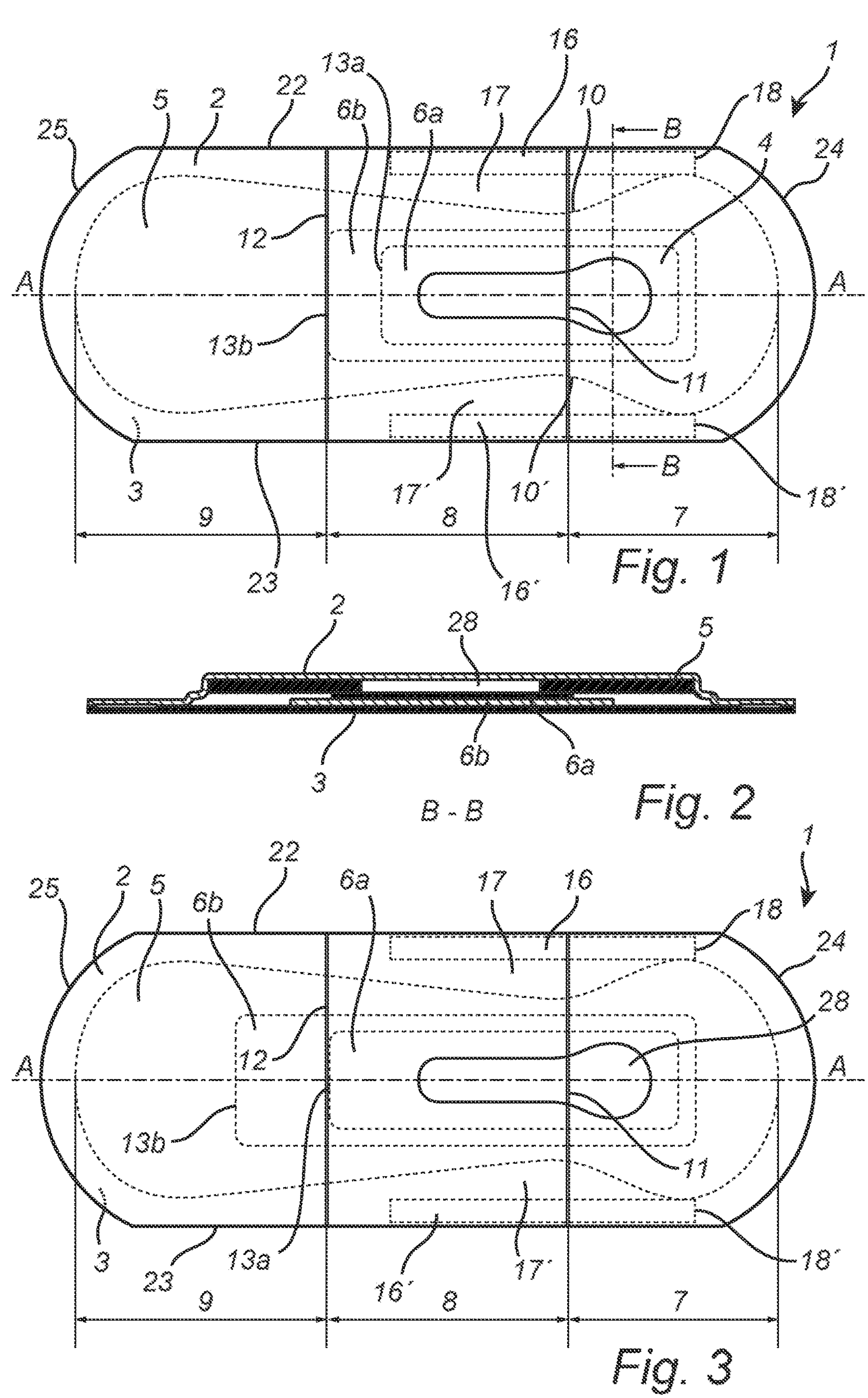
FIG. 1 is a top plan view of an exemplary absorbent article of the disclosure.
FIG. 2 is a cross-sectional view along the line B-B of the absorbent article of FIG. 1.
FIG. 3 is a top plan view of an exemplary absorbent article of the disclosure.

The disclosure will be described more closely below by an exemplary embodiment. The disclosure may however be embodied in many different forms and should not be construed as limited to the embodiments set forth in the drawings and the description thereto.

FIG. 1 schematically shows an absorbent article 1 in the form of an incontinence pad seen from the side that is intended to be facing towards a wearer's body when the article 1 is being worn. The article 1 has two longitudinal side edges 22, 23 having equal length and extending generally in the same direction. Front and rear end edges 24, 25 extend transversely at the ends of the article 1. The rear end edge 25 is intended to be oriented rearwards during use of the article 1, and the front-end edge 24 is intended to be facing forwards towards the abdomen of the wearer. The article 1 comprises a fluid permeable topsheet 2, a fluid impermeable backsheet 3 and an absorbent core 4 comprising three core layers 5, 6*a* and 6*b*. An upper core layer 5 is located between the topsheet 2 and the underlying core layer in the form of a fluid flow control structure 6*a*. The fluid flow control structure 6*a* is located between the upper core layer 5 and an underlying core layer in the form of a fluid storage structure 6*b* located between the fluid flow control structure 6*a* and the backsheet 3. The absorbent core 4 is in its longitudinal direction divided into a front portion 7, an intermediate portion 8 and a rear portion 9 by a first transverse fold line 11 and a second fold line 12, about which fold lines 11,12 the absorbent article 1 is intended to be folded prior to packaging the folded articles in a package comprising a plurality of folded articles. The upper core layer 5 extends over the front 7, the intermediate 8 and the rear portion 9 of the absorbent core 4. The flow control structure 6*a* partly extends over the front and intermediate portions 7,8 of the absorbent core 4. A rear end edge 13*a* of the flow control structure 6*a* is located in the intermediate portion 8 of the absorbent core 4. The fluid storage layer 6*b* extends over the intermediate portion 8 and partly over the front portion 4. A rear end edge 13*b* of the fluid storage layer 6*b* is arranged at the second fold line 12. The absorbent core 4 has a narrow transversal width 10-10' between the front portion 7 and the intermediate portion 8 of the core 4, the narrow transversal width 10-10' coincides with the first fold line 11. The upper core layer 5 and the fluid storage layer 6*b* may for example comprise a mixture of superabsorbent particles and pulp fibers. The fluid flow control structure may for example be a layered structure comprising a non-perforated fibrous polymeric layer and a first perforated polymeric layer, wherein the polymers in the first perforated polymeric layer are selected from polyolefins, polyesters, polyamides and blends and combinations thereof. The first perforated polymeric layer may have a basis weight of from 50 g/m2 to 150 g/m2, or a basis weight of from 60 g/m2 to 140 g/m2. The first perforated polymeric layer may be a nonwoven, a film or a film/nonwoven laminate. The first perforated polymeric layer may for example be a three-dimensionally formed layer having penetrating apertures. The non-perforated fibrous polymeric layer may be a high loft material of 50 g/m2 to 150 g/m2 or a basis weight of from 60 g/m2 to 140. The polymer for the non-perforated fibrous polymeric layer may be polyester. The fluid flow control structure may also be a three layer structure consisting of the non-perforated fibrous polymeric layer, the first perforated polymeric layer and a second perforated polymeric layer. The non-perforated fibrous polymeric layer may be sandwiched between the first perforated polymeric layer and the second perforated polymeric layer. The second perforated polymeric layer may also be a three-dimensionally formed layer having apertures extending from a first surface of the web towards a second surface of the web and forming protrusions on the second surface.

The upper core layer 5 has an opening 28 extending completely through the layer 5. The upper core layer 5 may have one or more openings 28 of different shapes and configurations. One elongated opening 28 is however preferred. The upper layer 5 may of course be a uniform layer without any larger openings. The opening 28 in the upper core layer 5 is arranged in the front and intermediate portions 7,8 of the upper core layer 5, about 5 to 10% of the longitudinal extension of the opening 28 is located in the front portion 7 of the upper core layer 5. The maximum transverse extension of the opening 28 is larger in the front portion 7 of the upper core layer 5 than the maximum transverse extension of the opening 28 in the intermediate portion 8 of the upper core layer 5. The opening 28 will in use of the article 1 be placed directly beneath the urethra and the vaginal opening of a female wearer. Any body fluid that is released to the absorbent article 1 will directly be collected in the opening 28 and be temporarily contained therein until it is distributed further into and throughout the absorbent core 4.

The topsheet 2 and the backsheet 3 extends together laterally outside the absorbent core 4 along the whole circumference and are connected to each other in an edge join around the periphery of the article 1. The edge join may be formed in any suitable manner as known in the art such as by adhesive, ultrasonic bonding, thermo-bonding etc. The topsheet 2 and the backsheet 3 may consist of any material suitable, such as nonwoven or film material, for the purpose as disclosed herein.

Elastic members 16, 16', such as band of elastic material, e.g., foam elastics, are arranged between the topsheet 2 and the backsheet 3 and along the longitudinal side edges 22, 23 of the article 1. The article has an interspace 17, 17' free from absorbent material located laterally between the elastic member 16, 16' and the transition between the front portion 7 and the intermediate portion 8 of the core 4. Each elastic member extends to a lateral edge 18, 18' of the widest part of the front portion 7 of the absorbent core 4.

FIG. 2 is a cross-sectional view along the line B-B of the absorbent article 1 in FIG. 1.

FIG. 3 illustrates an absorbent article 1 in the form of an incontinence pad, as seen from the side that is intended to be facing towards a wearer's body when the article 1 is being worn. The article 1 has two longitudinal side edges 22, 23 having equal length and extending generally in the same direction. Front and rear end edges 24, 25 extend transversely at the ends of the article 1. The rear end edge 25 is intended to be oriented rearwards during use of the article 1, and the front-end edge 24 is intended to be facing forwards towards the abdomen of the wearer. The article 1 comprises a fluid permeable topsheet 2, a fluid impermeable backsheet 3 and an absorbent core 4 comprising three core layers 5, **6*a* and 6*b*. An upper core layer 5 is located between the topsheet 2 and a fluid flow control structure 6*a*. The fluid flow control structure 6*a* is located between the upper core layer 5 and a fluid storage structure 6*b*. The absorbent core 4 is in its longitudinal direction divided into a front portion 7, an intermediate portion 8 and a rear portion 9 by a first transverse fold line 11 and a second fold line 12, about which fold lines 11,12 the absorbent article 1 is intended to be folded prior to packaging folded articles in a package comprising a plurality of folded articles. The upper core layer 5 extends over the front 7, the intermediate 8 and the rear portion 9 of the absorbent core 4. The flow control structure 6*a* extends over a part of the front portion 7 and over the intermediate portion 8 of the absorbent core 4. A rear end edge 13*a* of the flow control structure 6*a* is arranged at the second fold line 12. The fluid storage layer 6*b* extends over a part of the front portion 4, over the intermediate portion 8 and with a rear end edge 13*b* of the fluid storage layer 6*b* arranged at the rear portion 9 of the absorbent core 4. The absorbent core 4 has a narrow transversal width 10-10' between the front portion 7 and the intermediate portion 8 of the core 4, the narrow transversal width 10-10' coincides with the first fold line 11**.

The upper core layer 5 has an opening 28 extending completely through the layer 5. The upper core layer 5 may have one or more openings 28 of different shapes and configurations. One elongated opening 28 is however preferred.

Elastic members 16, 16' are arranged between the topsheet 2 and the backsheet 3 and along the longitudinal side edges 22, 23 of the article 1. The article has an interspace 17, 17' free from absorbent material located laterally between the elastic member 16, 16' and the transition between the front portion 7 and the intermediate portion 8 of the core 4. Each elastic member extends to a lateral edge 18, 18' of the widest part of the front portion 7 of the absorbent core 4.

Figures 4, 5A:
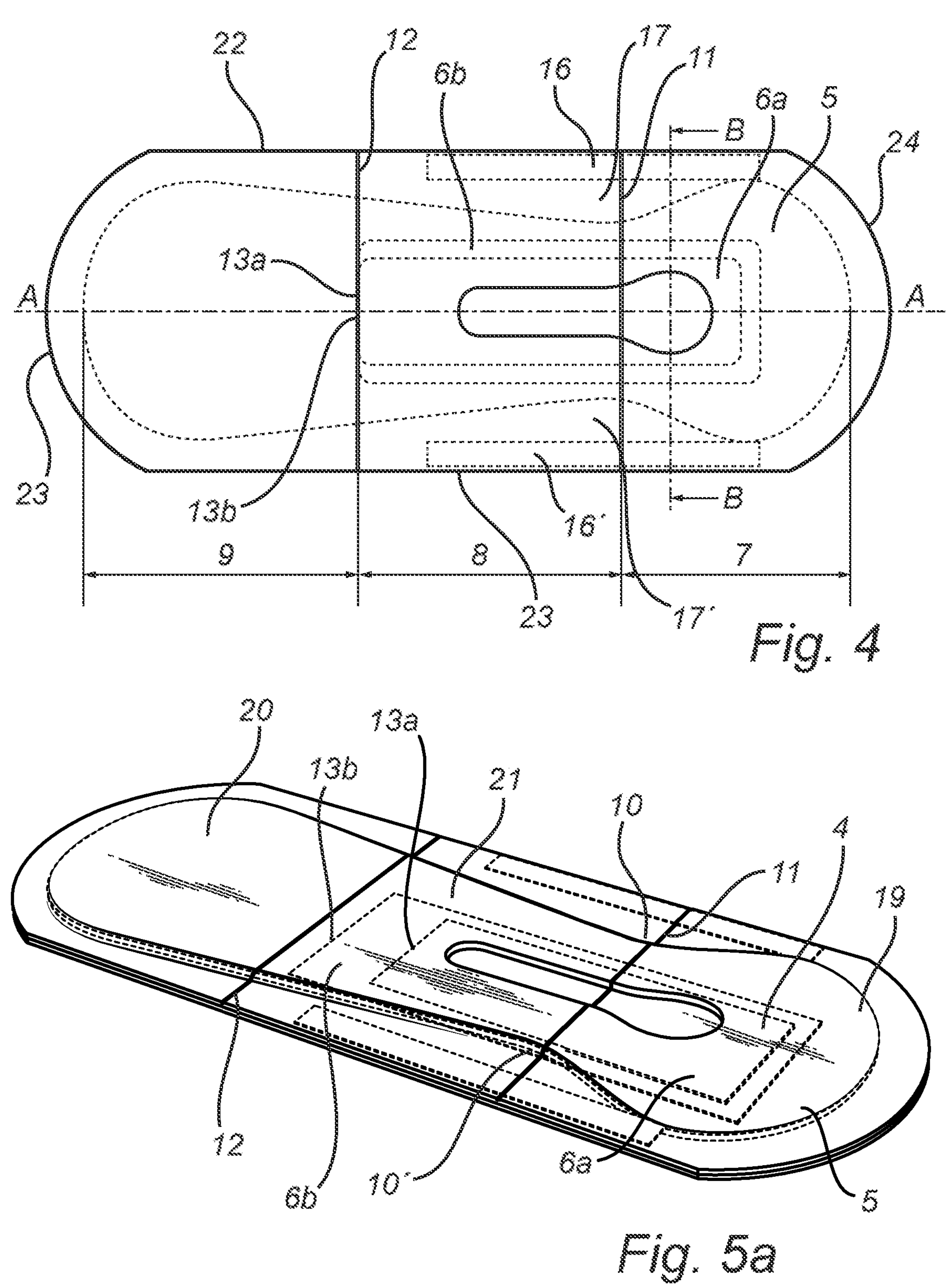
FIG. 4 is a top plan view of an exemplary absorbent article of the disclosure.
FIGS. 5*a*-5*d* are elevation views of successive steps of folding an absorbent article of FIG. 1.

FIG. 4 illustrates an absorbent article 1 according to the present disclosure comprising an absorbent 4 including an upper core layer 5 extending over the front, the intermediate 8 and the rear portion 9 of the absorbent core 4. The absorbent core 4 furthermore comprises a flow control structure **6*a* and a fluid storage layer 6*b*, both extending over a part of the front portion 7 and over the intermediate portion 8 with the rear end edges 13*a* and 13*b* respectively arranged at a second fold line 12. The absorbent core 4 has a narrow transversal width 10-10' between the front portion 7 and the intermediate portion 8 of the core 4, the narrow transversal width 10-10' coincides with a first fold line 11**.

Figures 5B, 5C, 5D:
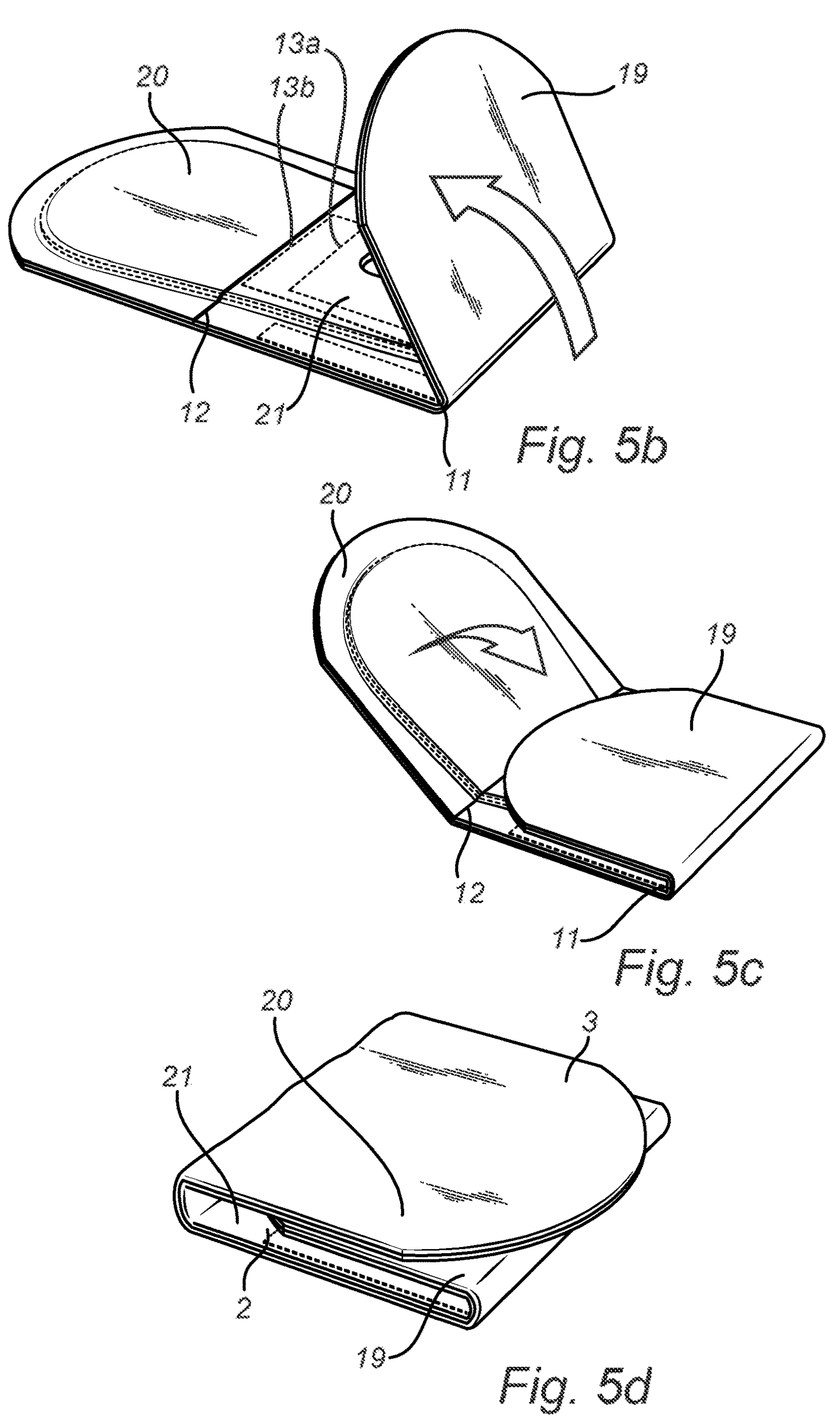

FIGS. **5*a* to 5*d* illustrate the two folding steps of the absorbent article 1 according to FIG. 1. Starting from FIG. 5*a* showing the unfolded article 1, the article 1 is divided into a first end portion 19, a second end portion 20 and a central area 21 by the first fold line 11 and the second fold line 12. In FIG. 5*b* the first end portion 19 of the article 1 is folded about the first transversal fold line 11 coinciding with or being adjacent the narrow transversal width 10-10' of the core 4, the article 1 is folded until the first end portion 19 is in contact with the central area 21 of the article 1, i.e., folding until topsheet 2 of the first end portion 19 is in contact with the topsheet 2 of the central area 21. In FIG. 5*c* the second end portion 20 of the article 1 is folded about the second transversal fold line 12 adjacent the rear transversal edge 13*b* of the fluid storage layer 6*b* until it is in contact with the portion 19 of the article 1 already folded, i.e., the topsheet 2 of the second end portion 20 is facing the backsheet 3 of the first end portion 19. FIG. 5*d* shows the final folded article 1**.

FIGS. **6*a* to 6*c* illustrate an alternative folding with two folding steps of the absorbent article shown in FIG. 6*a*. The article 1 comprising the upper core layer 5 and the two underlying core layers 6*a* and 6*b*. In FIG. 6*a* a second end portion 20 of the article 1 is folded in a first folding step about the second transversal fold line 12 adjacent the transversal edge 13*b* of the underlying core layer 6*b* until the second end portion 20 is in contact with the central area 21 of the article 1, i.e., folding until topsheet 2 of the second end portion 20 is in contact with the topsheet 2 of the central area 21. FIG. 6*b* illustrates the second folding step, wherein a first end portion 19 of the article 1 is folded about the first transversal fold line 11 until it is in contact with the portion 19 of the article 1 already folded, i.e., the topsheet 2 of the first end portion 19 is facing the backsheet 3 of the second end portion 20. FIG. 6*c* shows the final folded article 1**.

The invention claimed is:

1. A folded absorbent article comprising:

a fluid permeable topsheet, a backsheet, and an absorbent core comprising at least two core layers located between the topsheet and the backsheet, the at least two core layers including an upper core layer and one or more underlying core layers, the upper core layer being located between the topsheet and the one or more underlying core layers, the topsheet and the backsheet extending together laterally outside the absorbent core, the absorbent core in its longitudinal direction having a front portion, a rear portion and an intermediate portion located between the front portion and the rear portion, a transversal width of a transition between the front portion and the intermediate portion of the core being narrower than the transversal width of the rest of the core, a first end portion of the article being folded about a first transversal fold line over a central area of the article, the first fold line coinciding with or being adjacent the narrow transversal transition between the front portion and the intermediate portion of the core, wherein the upper core layer extends within the front, the intermediate and the rear portions of the absorbent core, wherein at least one of the one or more underlying core layers is shorter than the upper core layer and extends within the intermediate portion and at least a part of the front portion of the absorbent core, wherein a second end portion of the article is folded about a second transversal fold line over the central area of the article, the second fold line being at or adjacent a rear transversal edge of the at least one shorter underlying core layer, the second fold line coinciding with the transition between the intermediate portion and the rear portion, and wherein the first end portion is folded onto the central area and the second end portion is folded onto the first end portion or the second end portion is folded onto the central area and the first end portion is folded onto the second end portion.

2. The absorbent article according to claim 1, wherein the article is a sanitary napkin or pad.

3. The absorbent article according to claim 1, wherein the front portion, the rear portion and the intermediate portion of the absorbent core are of substantially equal length.

4. The absorbent article according to claim 1, wherein the front portion of the upper core layer constitutes 20-40% of the total longitudinal extension of the upper core layer.

5. The absorbent article according to claim 1, wherein the upper core layer has an opening extending there through.

6. The absorbent article according to claim 5, wherein the opening is arranged in the front portion and the intermediate portion of the absorbent core.

7. The absorbent article according to claim 5, wherein the longitudinal extension of the opening in the upper core layer is 20-40% of the longitudinal extension of the upper core layer.

8. The absorbent article according to claim 6, wherein a maximum transverse extension of the opening is larger in the front portion of the absorbent core than a maximum transverse extension of the opening in the intermediate portion of the absorbent core.

9. The absorbent article according to claim 1, wherein the absorbent core comprises two or more underlying core layers, one of the underlying core layers being a fluid flow control structure and one of the underlying core layers is a fluid storage structure, and wherein the fluid flow control structure is located between the upper core layer and the fluid storage structure.

10. The absorbent article according to claim 9, wherein the fluid control structure is one of the at least one underlying core layer being shorter than the upper core layer.

11. The absorbent article according to claim 9, wherein the fluid storage structure is one of the at least one underlying core layer being shorter than the upper core layer.

12. The absorbent article according to claim 1, wherein the transversal width of the transition between the front portion and the intermediate portion of the core is 50-75% of the greatest width of the front portion of the absorbent core.

13. The absorbent article according to claim 1, wherein an elastic member is arranged along each longitudinal side edge of the article, laterally outside of the absorbent core at least at the transition between the front portion and the intermediate portion of the core.

14. The absorbent article according to claim 13, wherein the article has an interspace free from absorbent material located between the elastic member and the transition between the front portion and the intermediate portion of the core.

15. The absorbent article according to claim 13, wherein each elastic member extends in the longitudinal direction at least to a lateral edge of a widest part of the front portion of the absorbent core.

16. The absorbent article according to claim 13, wherein no elastic member extends in the longitudinal direction beyond the rear transversal edge of the rear part of the upper core layer.

17. The absorbent article according to claim 1, wherein the surface area of the at least one of the underlying core layers which is shorter than the upper core layer is 30-60% of the surface area of the upper core layer.

18. A package comprising a plurality of folded absorbent articles according to claim 1.

19. The absorbent article according to claim 1, wherein the second end portion is folded onto the central area and the first end portion is folded onto the second end portion.

20. A method of folding an absorbent article, the article comprising a fluid permeable topsheet, a backsheet and an absorbent core comprising an upper core layer and one or more underlying core layers located between the topsheet and the backsheet, wherein the upper core layer being located between the topsheet and the one or more underlying core layers, the topsheet and the backsheet extending together laterally outside the absorbent core, the absorbent core in its longitudinal direction having a front portion, a rear portion and an intermediate portion located between the front portion and the rear portion, a transversal width of a transition between the front portion and the intermediate portion of the core being narrower than the transversal width of the rest of the core, the upper core layer extending within the front, intermediate and rear portions of the absorbent core, and at least one of the one or more underlying core layers is shorter than the upper core layer and extends within the intermediate portion and at least a part of the front portion of the absorbent core, the method comprising:

a) folding a first end portion of the article about a first transversal fold line onto a central area of the article, the first fold line coinciding with or being adjacent the narrow transversal transition between the front portion and the intermediate portion of the core, and, b) folding a second end portion of the article about a second transversal fold line onto the first folded end portion, the second fold line being at or adjacent a rear transversal edge of the at least one underlying core layer being shorter than the upper core layer.

21. The method according to claim 20, wherein each of the one or more underlying core layers is shorter than the upper core layer and extends over the front portion and the intermediate portion of the absorbent core and wherein the second fold line is adjacent the rear transversal edge of each of the underlying core layers.

22. A method of folding an absorbent article, the article comprising a fluid permeable topsheet, a backsheet and an absorbent core comprising an upper core layer and one or more underlying core layers located between the topsheet and the backsheet, wherein the upper core layer being located between the topsheet and the one or more underlying core layers, the topsheet and the backsheet extending together laterally outside the absorbent core, the absorbent core in its longitudinal direction having a front portion, a rear portion and an intermediate portion located between the front portion and the rear portion, a transversal width of a transition between the front portion and the intermediate portion of the core being narrower than the transversal width of the rest of the core, the upper core layer extending within the front, intermediate and rear portions of the absorbent core, and at least one of the one or more underlying core layers being shorter than the upper core layer and extends within the intermediate portion and at least a part of the front portion of the absorbent core, the method comprising:

a) folding a second end portion of the article about a second transversal fold line onto a central area of the article, and b) folding a first end portion of the article about a first transversal fold line onto the second folded end portion, the first fold line coinciding with or being adjacent the narrow transversal transition between the front portion and the intermediate portion of the core, wherein, the second fold line is at or adjacent a rear transversal edge of the at least one of the one or more underlying core layers being shorter than the upper core layer.

* * * * *